(12) United States Patent
Schreiber

(10) Patent No.: US 9,170,410 B2
(45) Date of Patent: Oct. 27, 2015

(54) APPARATUS FOR TEMPORAL DISPLACEMENT OF WHITE LIGHT LASER PULSES

(75) Inventor: Frank Schreiber, Dossenheim (DE)

(73) Assignee: Leica Microsystems CMS GmbH, Wetzlar (DE)

(*) Notice: Subject to any disclaimer, the term of this patent is extended or adjusted under 35 U.S.C. 154(b) by 690 days.

(21) Appl. No.: 13/219,357

(22) Filed: Aug. 26, 2011

(65) Prior Publication Data

US 2012/0050849 A1   Mar. 1, 2012

(30) Foreign Application Priority Data

Aug. 27, 2010   (DE) .......................... 10 2010 037 190

(51) Int. Cl.
| | |
|---|---|
| G02B 21/06 | (2006.01) |
| G02B 21/00 | (2006.01) |
| G02B 21/16 | (2006.01) |
| G01N 21/64 | (2006.01) |
| H01S 3/00 | (2006.01) |

(52) U.S. Cl.
CPC ............ *G02B 21/0032* (2013.01); *G02B 21/16* (2013.01); *G01N 21/6408* (2013.01); *G01N 21/6458* (2013.01); *G02B 2207/117* (2013.01); *H01S 3/0057* (2013.01)

(58) Field of Classification Search
CPC .... G02B 21/06; G02B 21/16; G02B 21/0076; G02B 21/0032; G02B 21/6458
USPC ............... 359/385, 337.5, 349, 362, 368, 359/388–390, 337.1, 337.2, 337.21, 615, 359/577, 589, 637, 634, 837; 372/1–3, 5–8, 372/38.02, 50.12, 71
See application file for complete search history.

(56) References Cited

U.S. PATENT DOCUMENTS

| | | | |
|---|---|---|---|
| 4,972,423 | A | 11/1990 | Alfano et al. |
| 5,184,251 | A | 2/1993 | Tsuchida et al. |
| 5,995,281 | A | 11/1999 | Simon et al. |
| 7,519,096 | B2 * | 4/2009 | Bouma et al. ................. 372/102 |
| 7,593,434 | B2 | 9/2009 | Liu et al. |
| 7,593,441 | B2 | 9/2009 | Brennan, III et al. |

(Continued)

FOREIGN PATENT DOCUMENTS

| | | |
|---|---|---|
| DE | 1 096 634 | 7/1959 |
| DE | 196 22 359 B4 | 12/1997 |

(Continued)

OTHER PUBLICATIONS

European Search Report dated Dec. 2, 2011 including English translation (Seven (7) pages).

(Continued)

*Primary Examiner* — Scott J Sugarman
*Assistant Examiner* — Tamara Y Washington
(74) *Attorney, Agent, or Firm* — Crowell & Moring LLP (57) ABSTRACT

A laser microscope (10) having a laser light source (22) which generates laser light pulses (23) for the purpose of examining a sample (16). An optical element (25) is arranged in the beam path of the laser light pulses (23). The optical element (25) disperses the wavelength spectrum of the laser light pulses (23). Fractions (46, 48, 60, 62) of the broad-band laser light pulses (32) having different wavelengths travel different path lengths upon passing through a compensation device (30), such that the different fractions (46, 48, 60, 62) arrive at the sample (16) at the same time.

7 Claims, 6 Drawing Sheets

(56) References Cited

U.S. PATENT DOCUMENTS

| | | |
|---|---|---|
| 7,777,940 B1 | 8/2010 | Delfyett et al. |
| 7,817,680 B2 | 10/2010 | Liu et al. |
| 7,822,347 B1 | 10/2010 | Brennan, III et al. |
| 7,995,271 B2 | 8/2011 | Kubo |
| 7,995,627 B2 * | 8/2011 | Bouma et al. ............... 372/20 |
| 2002/0009260 A1 | 1/2002 | Birk et al. |
| 2002/0067747 A1 | 6/2002 | Jalali et al. |
| 2005/0078363 A1 | 4/2005 | Gugel |
| 2006/0012871 A1 * | 1/2006 | Funk et al. ............... 359/385 |
| 2006/0203354 A1 | 9/2006 | Fujimoto et al. |
| 2006/0237666 A1 | 10/2006 | Kubo |
| 2007/0025662 A1 | 2/2007 | Gugel |
| 2008/0043789 A1 | 2/2008 | Moro et al. |
| 2009/0097512 A1 | 4/2009 | Clowes et al. |
| 2010/0134793 A1 | 6/2010 | Krishnamachari et al. |
| 2010/0177378 A1 | 7/2010 | Kondo et al. |
| 2010/0187438 A1 | 7/2010 | Hell et al. |
| 2011/0062348 A1 | 3/2011 | Matthae et al. |

FOREIGN PATENT DOCUMENTS

| | | |
|---|---|---|
| DE | 103 13 987 B4 | 10/2004 |
| DE | 103 40 964 A1 | 3/2005 |
| DE | 103 47 712 A1 | 5/2005 |
| DE | 60 2005 003 947 T2 | 12/2008 |
| DE | 10 2007 048 135 A1 | 4/2009 |
| DE | 10 2008 022 493 A1 | 11/2009 |
| DE | 10 2008 059 579 A1 | 7/2010 |
| EP | 1 986 030 A1 | 10/2008 |
| GB | 2 410 122 A | 7/2005 |
| WO | WO 2007/050743 A2 | 5/2007 |
| WO | WO 2008/009581 A1 | 4/2008 |
| WO | WO 2009/144635 A2 | 12/2009 |

OTHER PUBLICATIONS

German Office Action dated Jan. 17, 2011 (four (4) pages).

* cited by examiner

APPARATUS FOR TEMPORAL DISPLACEMENT OF WHITE LIGHT LASER PULSES

BACKGROUND OF THE INVENTION

The invention relates to a laser microscope for examining a sample. The laser microscope has a laser light source which generates laser light pulses. An optical element disperses the spectrum of the laser light pulses. The latter are termed broadband laser light pulses below.

Pulsed laser light is usually used in laser microscopes for measuring intracellular ion concentrations. In this case, the process is based on the discovery that the fluorescence lifetime—that is, the average duration for which the electrons remain in the excited state—changes with ion concentration. A corresponding method is, for example, fluorescence lifetime imaging (FLIM). The pulse durations of the laser light pulses necessary in this case are in the range of picoseconds, for example.

For the purpose of examining the fluorescence lifetime of different dyes, the sample must frequently be excited with laser light pulses of varying wavelength. For this purpose, various lasers are provided which each generate laser light pulses of one wavelength or of a very small wavelength region. Due to the different propagation speeds of laser light of different wavelengths in media, resonators in laser light sources commonly have compensation elements which function to make the laser light pulses of differing wavelengths leave the laser at the same time. The time spans being compensated in such cases are in the range of femtoseconds.

U.S. Pat. No. 5,995,281 (=DE 196 22 359) discloses a device for coupling the beam of short-pulse lasers into a microscopic beam path, wherein the coupling is achieved by at least one fiber optic waveguide arranged downstream from the laser.

German patent no. DE 103 13 987 B4 discloses a device for illuminating an object. The light of a light source is coupled into a micro-structured element which disperses the spectrum of the light.

U.S. Pat. No. 7,995,271 (=EP 1 986 030) discloses a laser microscope which has a laser light source. The laser light is coupled into a first and a second fiber optic waveguide.

SUMMARY OF THE INVENTION

The problem addressed by the present invention is that of creating a laser microscope which enables the precise measurement of the fluorescence lifetime of differing fluorescent dyes, wherein said measurements are simultaneously especially simple.

This and other objects of the invention are achieved by the invention as described and claimed hereinafter.

The invention is characterized by a compensation device in which fractions of the broadband laser light pulses having different wavelengths travel different path lengths, such that the different fractions arrive at the sample at the same time.

As is known, light of different wavelengths has different propagation speeds in a medium. Particularly, the fraction of the laser light pulses having different wavelengths have different propagation speeds inside the optical element. This has the consequence that the optical element not only spectrally disperses the laser light pulse, but also temporally displaces the fractions of the laser light pulses which have different wavelengths with respect to each other, such that afterwards time delays or differing passage times appear between the different fractions. These differences in passage time and/or displacement can be in the range of nanoseconds. The conventional compensation elements in the resonators of the laser are not suited in principle for compensating such large time delays. The compensation device according to the invention now compensates these differences in passage time by the fact that the different fractions travel different path lengths in the compensation device. This enables the measurements of fluorescence lifetime to be carried out in a particularly simple manner, because only one single laser light source must be provided, while the fluorescence lifetime of different dyes can be measured at the same time. In this context, the fact that the different fractions of the light arrive at the sample at the same time means that the light pulses of differing wavelength, each having a pulse duration, at least temporally overlap with each other. The compensation is preferably carried out by utilizing the compensation device in such a manner that the light pulses arrive at the sample at the same time, and therefore the illumination by means of light pulses having differing wavelengths begins at the same time. As an alternative or in addition thereto, the pulse durations can also further be adjusted to each other such that the illumination by light pulses of differing wavelengths ends at the same time.

According to one embodiment, the path length traveled by one of the fractions inside the compensation device is variable. For this purpose, an adjustable mirror is provided, for example, wherein the position thereof affects the path length.

In a further embodiment, a difference between two path lengths traveled by two different fractions of the laser light in the compensation device is discrete. In this context, this means that, by way of example, fractions of adjacent wavelengths travel significantly different path lengths in the compensation device, said path lengths having a discrete spacing from each other. This enables the differences in passage time to be compensated in the nanosecond range.

According to a further embodiment, the laser light is split into a first fraction having a first wavelength, and a second fraction having a second wavelength. At least one of the two wavelengths is variable. In other words, the wavelength of at least one of the fractions of the laser light can be set and/or selected. For this purpose, an adjustable mirror can be provided, for example, wherein the position thereof has an affect on the wavelength of the corresponding fraction.

According to a further embodiment, a sensor device is provided which detects the difference in passage time between the different fractions. An adjuster device adjusts the path length traveled by at least one of the fractions in the compensation device according to the difference in passage time, such that the laser pulses of differing wavelengths arrive at the same time.

In a further embodiment, after traveling the different path lengths, the different fractions are parallel and displaced with respect to the different fractions before the same have traveled the different path lengths. This displacement—that is, the separation between the light pulses entering the compensation device and those exiting the compensation device—can be achieved by using a mirror arrangement, for example, wherein the same have multiple mirrors which are tilted with respect to each other, for example. For example, one or more mirrors, the same being used to provide the differing path lengths, can be designed in such a manner—for example as 90° double mirrors—that the reflected fractions of light are both parallel to and displaced with respect to the fractions of light entering the device.

The path lengths are geometric or optical path lengths. In other words, the path lengths can be varied when the light travels different path lengths—that is, different geometric path lengths—and/or when the light passes through different media—that is, travels different optical path lengths. For the purpose of adjusting the different path lengths, the compensation device can have one or more mirrors, as well as one or more prisms, wherein the positions of the same affect the path lengths.

BRIEF DESCRIPTION OF THE DRAWINGS

The invention will be described in further detail hereinafter with reference to illustrative embodiments shown the accompanying drawing figures in which.

In the drawings elements having the same construction or function are designated by the same reference numbers in all figures.

DETAILED DESCRIPTION OF PREFERRED EMBODIMENTS

Figure 1:
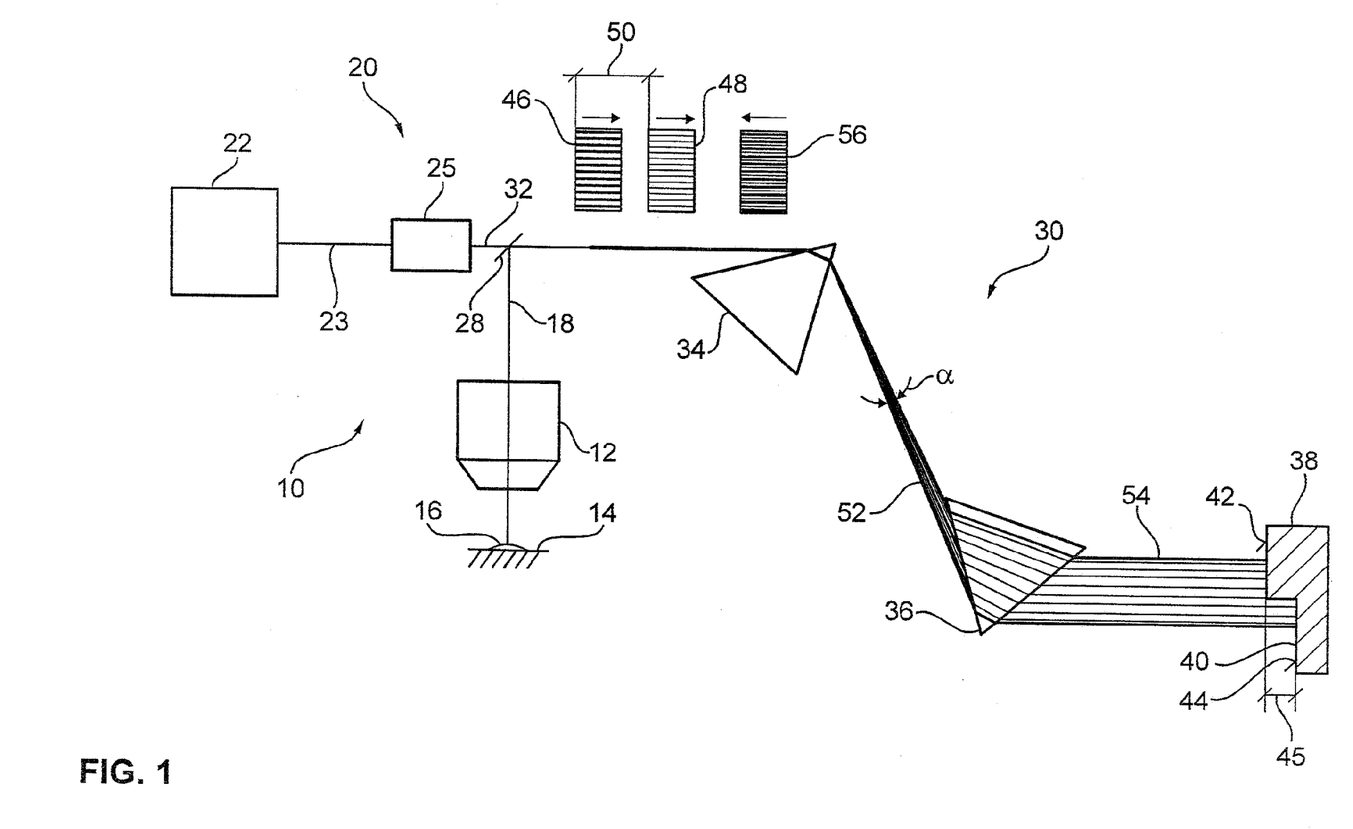
FIG. 1 shows a laser microscope having one embodiment of a compensation device according to the invention.

FIG. 1 shows a laser microscope 10 which enables the observation of a sample 16 lying on a sample platform 14 by means of a lens 12. For this purpose, the sample 16 is illuminated with an illuminating light beam 18. The illuminating light beam 18 is initially generated by the production of laser light pulses 23 by means of a laser light source 22. The laser light pulses 23 have a single wavelength or an extremely narrow wavelength band. For this reason, the laser light pulses 23 are also termed narrow-band laser light pulses 23. The laser light source 22 has a pulsed titanium sapphire laser, for example, or a laser diode. The laser microscope 10 is suitable for measuring fluorescence lifetimes of fluorescing dyes. The laser microscope 10 can be a confocal microscope and/or a scanning microscope. In the figures, the characteristic components, such as a detection pinhole and/or a scanning unit, for example, are not illustrated.

The narrow-band laser light pulses 23 are directed onto an optical element 25, and penetrate the optical element 25. The optical element 25 is micro-structured and disperses the wavelength spectrum of the laser light pulses 23. The dispersal of the wavelength spectrum is the result of non-linear optical effects in the optical element 25. Such spectrally dispersed laser light is termed broadband laser light, broad-band laser light, or white light. The unit composed of the laser light source 22 and the optical element 25 can also be termed the white light laser. As such, broad-band laser light pulses 32 exit the optical element 25.

In addition to the dispersal of the wavelength spectrum of the laser light pulses 23, the optical element 25 functions to temporally displace the fractions of the broad-band laser light pulses 32 having different wavelengths with respect to each other.

Differences in passage time, a phase shift, and/or a temporal displacement between laser light pulses of differing wavelengths are created in this way. In addition, the pulse durations of the light pulses can be extended to differing degrees.

A compensation device 30 for the purpose of compensating the temporal displacement, the difference in passage time, and/or the pulse durations has a first prism 34, a second prism 36, and a stepped reflector 38. The broad-band laser light pulses 32 arrive at a first beam splitter 28 and pass through the same in the direction of the first prism 34. The first prism 34 divides the broad-band laser light pulses 32 according to the wavelengths thereof, such that a beam fan 52 is generated between the first prism 34 and the second prism 36. The beam fan 52 has a flare angle α. The second prism 36 functions to make the spectrally divided laser light pulses 54 arrive at the step reflector 38 parallel to each other.

The step reflector 38 has a step 40. The step reflector 38 has a first mirror surface 42 above the step 40. Long-wave fractions of the spectrally divided laser light pulses 54 arrive at said mirror surface 42. A second mirror surface 44 is constructed on the step 40, and short-wave fractions of the spectrally divided laser light beams 54 arrive at said mirror surface 44. The step 40 has a step height 45. Because of the two prisms 34, 36, the path length traveled by a fraction of the laser light pulses 32 in the compensation device 30 changes continuously with the wavelength of the respective fraction. Because of the step reflector 38, the traveled path length changes discretely from one fraction having a first wavelength to another fraction having a second wavelength, particularly by the double of the step height 45. The path lengths for the different fractions therefore change not only continuously, but also discretely. This discrete path length difference enables the compensation, in nanoseconds, of passage time differences.

The broad-band laser light pulses 32 have a first light packet 46 with light of relatively long wavelengths, and a second light packet 48 with light of relatively short wavelengths. The light packages 46, 48 can also be characterized as fractions of the broad-band laser light pulses 32. A passage time difference 50 results between the two light packets 46, 48. The path lengths traveled by the different fractions are set by means of the prisms 34, 36 and the step reflector 38 in such a manner that a combined light packet 56 reflected by the step reflector 38 has light of different wavelengths which arrive at the sample at the same time, and particularly the first light packet 46 and the second light packet 48 are mixed, and arrive at the sample at the same time. The light packets 46, 48 represent individual broad-band laser light pulses 32. As such, the laser light pulses of differing wavelengths arrive at the sample 16 at the same time. The compensation device 30 consequently enables the compensation of the difference in passage time 50, the same resulting from the dispersal of the wavelength spectrum of the laser light pulses 23 by means of the optical element 25, particularly for the reason that light fractions having different wavelengths travel discretely different path lengths.

The fact that the light pulses arrive at the sample at the same time means that the light pulses at least overlap temporally with each other at the sample. However, the term "at the same time" preferably also means that the light pulses arrive at the sample in such a way that the illumination of the same by means of light pulses having different wavelengths begins at the same time. In addition, the term "at the same time" can also mean that the illumination by means of the light pulses ends at the same time, or the pulse durations of the light pulses have equals lengths. As an alternative, the term "at the same time" can also mean that the illumination by means of the light pulses ends at the same time, or the pulse durations of the light pulses have equals lengths.

Figure 2:
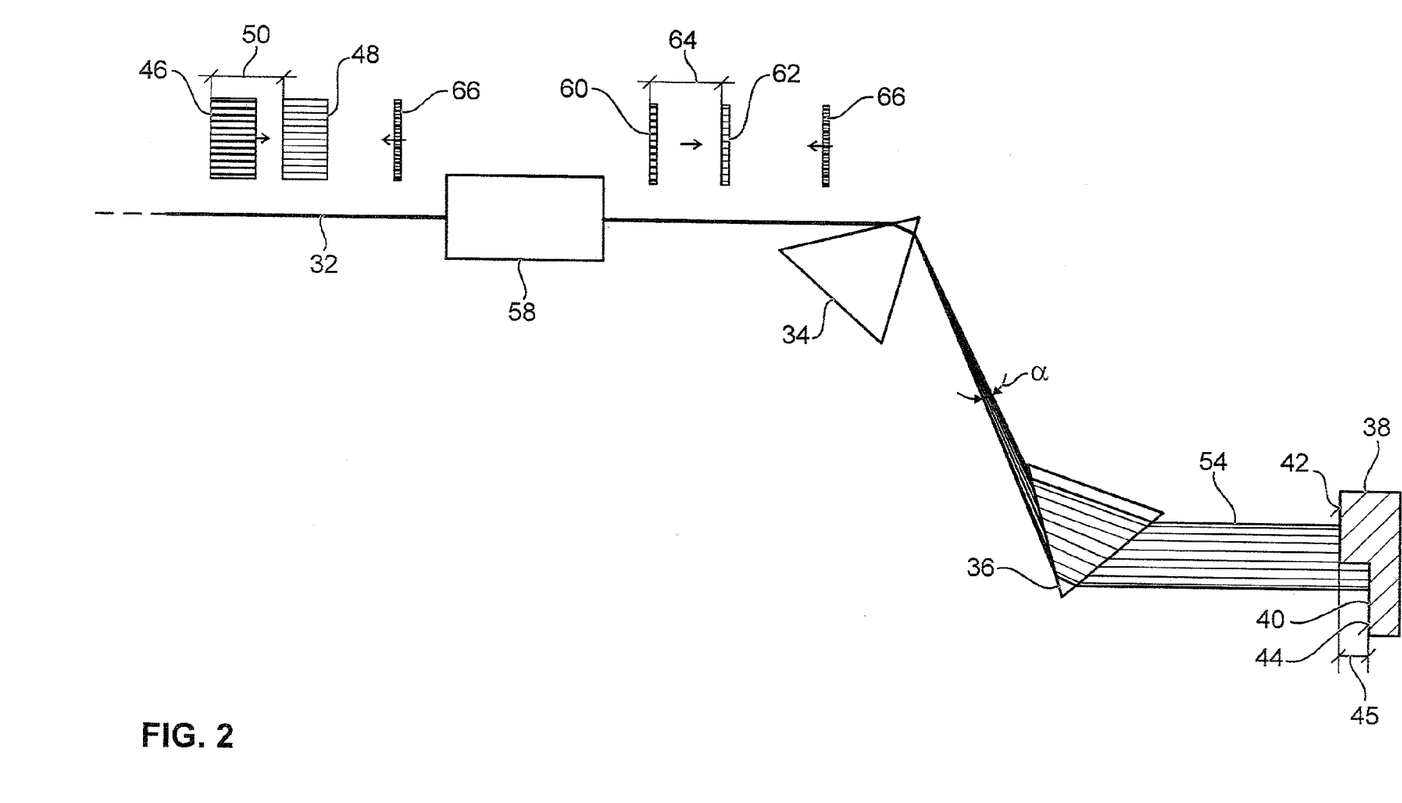
FIG. 2 shows a second embodiment of the compensation device.

FIG. 2 shows an alternative embodiment of the compensation device 30. In this embodiment, the broad-band laser light pulses 32 arrive at a first filter 58. The first filter 58 is an acousto/optical filter (AOTF), by way of example. The acousto/optical filter filters a first fraction 60 having a first wavelength, and a second fraction 62 having a second wavelength out of the broad-band laser light pulses 32, and the same have a further difference in passage time 64 with respect to each other. The magnitude of the further difference in passage time 64 substantially depends on the wavelength region of both fractions 60, 62. The larger the difference between the wavelength regions, the larger the further difference in passage time 64 is. According to the embodiment in FIG. 1, because of the two prisms 34, 36 and the step reflector 38, a path length difference results for both fractions 60, 62 upon passage of the same through the compensation device 30. Particularly, a discrete path length difference results which corresponds to the further difference in passage time 64. After passage through both prisms 34, 36 and reflection at the step reflector 38, no difference in passage time and no temporal displacement exists any more between the fractions 60, 62 representing the individual light pulses, such that the mixed fractions 66 pass through the first filter 58 together and arrive at the sample 16 at the same time. Said sample is not portrayed in this figure.

Figure 3:
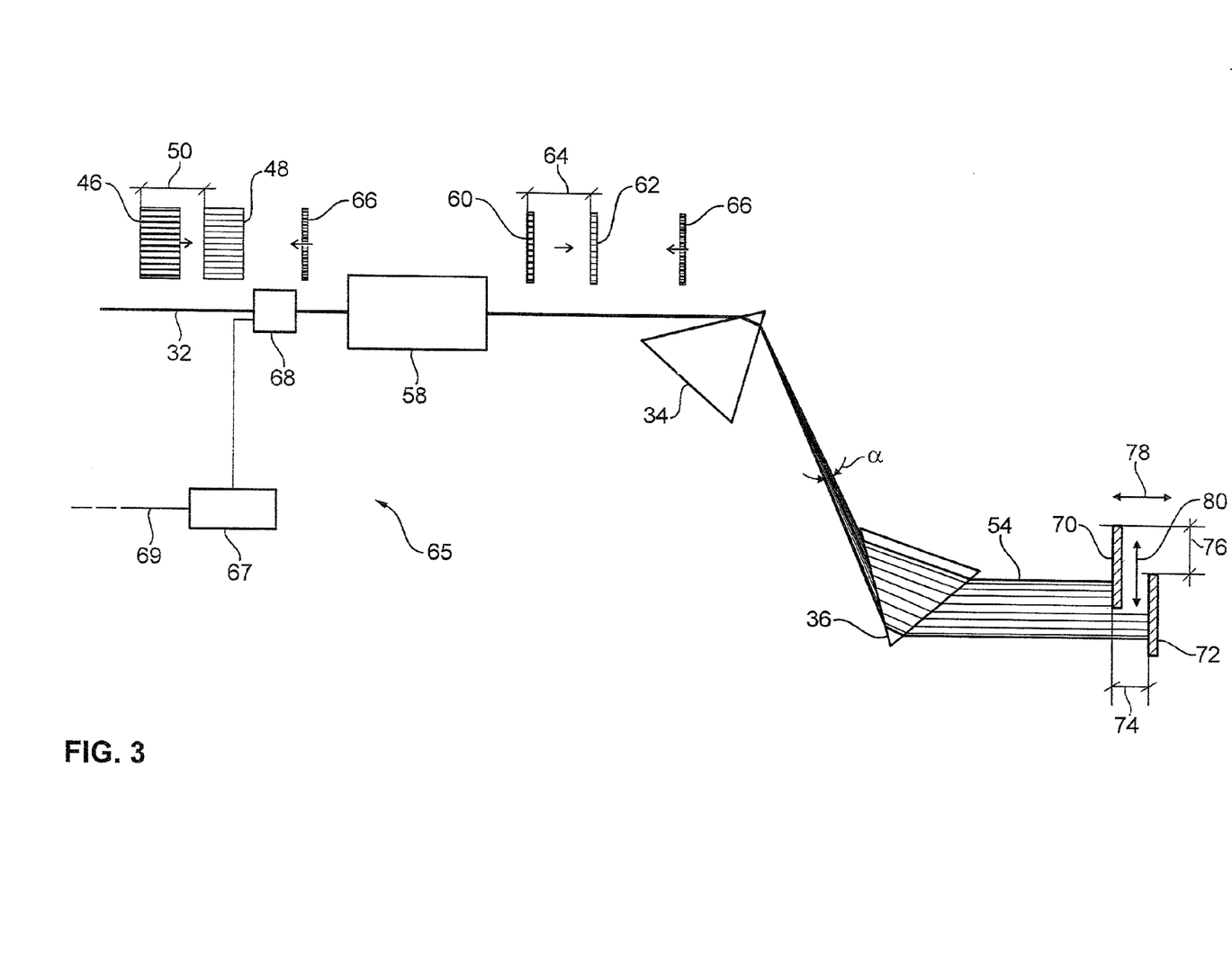
FIG. 3 shows a third embodiment of the compensation device.

FIG. 3 shows an embodiment of the compensation device 30 together with a sensor device 65. The sensor device 65 has a sensor 68 which is arranged in the beam path of the broadband laser light pulses 32. In addition to the illustration as given, the sensor 68 can also be positioned in other locations, for example behind the filter 58. The sensor 68 detects the differences in passage time between laser light pulses of differing wavelengths. The sensor 68 is read out by means of a control device 67. The control device 67 determines different path lengths for different fractions of the laser light pulses from the detected differences in passage time 50, 64. In addition, the control device 67 determines actuating parameters for adjusting component assemblies, wherein the path lengths can be adjusted by means of said component assemblies. Such component assemblies are, by way of example, a first adjustment mirror 70 and a second adjustment mirror 72.

The broad-band laser light pulses 32 pass through the first filter 58. This filters the first and the second fractions 60, 62 out of the broad-band laser light pulses 32. Both fractions 60, 62 penetrate both prisms 34, 36 in the direction toward the first and second adjustment mirrors 70, 72. The first adjustment mirror 70 has a first spacing 74 from the second adjustment mirror 72, defined in the direction of propagation of the spectrally divided laser light pulses 54. The first adjustment mirror 70 has a second spacing 76 from the second adjustment mirror 72 in the dimension defined perpendicular to the direction of propagation. Both adjustment mirrors 70, 72, or at least one of the two adjustment mirrors 70, 72 can be moved by means of adjustment devices in a first direction of movement 78 parallel to the direction of propagation, and/or in a second direction of movement 80 which is perpendicular to the direction of propagation. Said adjustment devices are not illustrated.

The first spacing 74 affects a path length traveled by light pulses having a prespecified wavelength, and therefore affects a passage time of the same light pulses. In this case, a discrete difference in the path lengths or passage times between light pulses of differing wavelengths can be adjusted by means of the adjustment devices.

The second spacing 76 affects which fractions of the broad-band laser light pulses 32 travel which path lengths. Particularly, the second spacing 76 determines which fractions 60, 62 of the broad-band laser light pulses 32 travel a longer path length, and which travel a shorter path length. As such, the path lengths traveled by the fractions 60, 62 can be changed by means of the sensor device 65, and according to the further difference in passage time 64, in such a manner, and the wavelengths thereof can be restricted in such a manner, that a fraction 66 which is mixed with respect to the wavelengths thereof passes through the first filter 58 while traveling on its reflected path, and is deflected toward the sample 16. The mixed fraction 66 represents a single laser light pulse having light of differing wavelengths.

Figure 4:
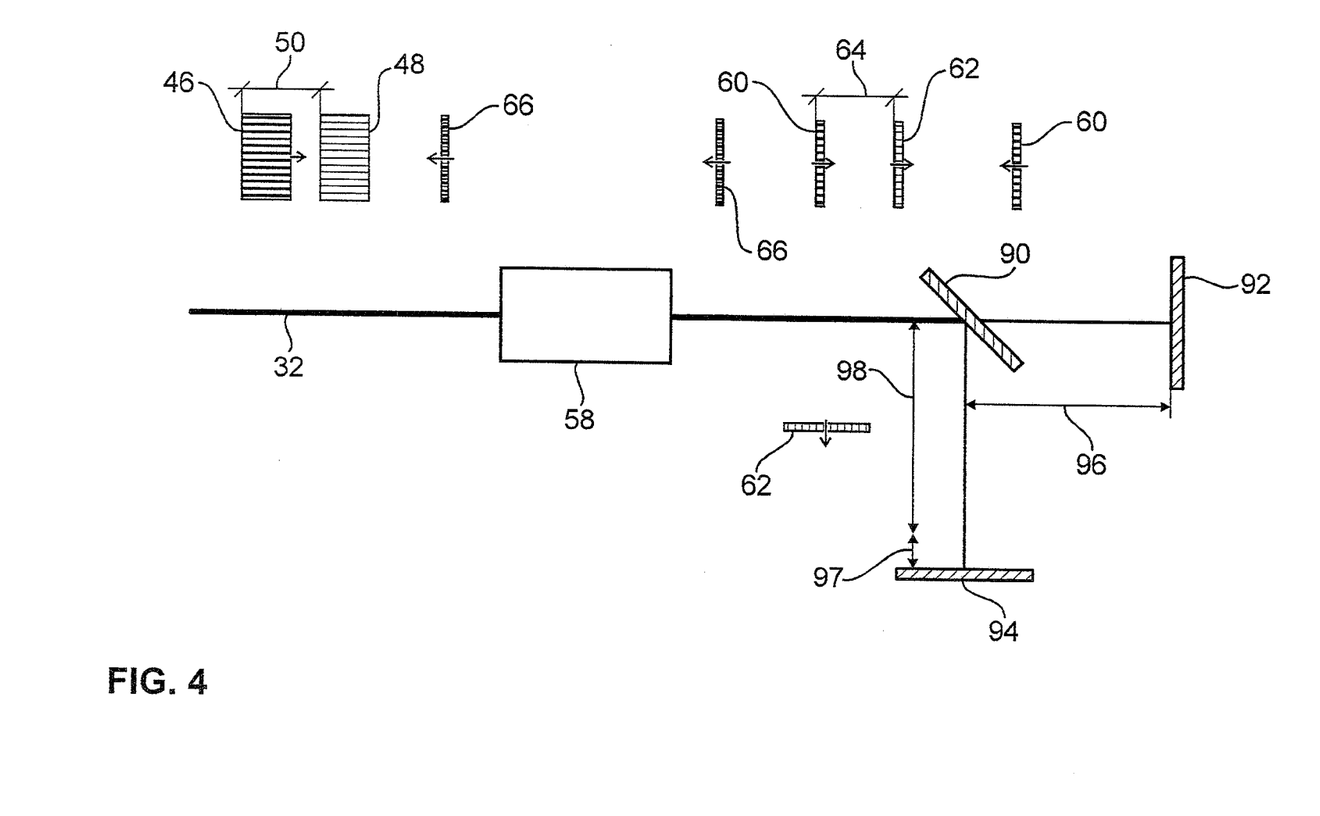
FIG. 4 shows a fourth embodiment of the compensation device.

FIG. 4 shows an alternative embodiment of the compensation device 30, wherein particularly the manner in which the path length is varied is different than in the case of the embodiments named above. Otherwise, this embodiment of the compensation device 30 corresponds to the embodiments named above. The fractions 60, 62 exit the first filter 58. The fractions 60, 62 arrive at a second beam splitter 90, and the latter deflects the second fraction 62 toward a first adjustment reflector 94, and allows the first fraction 60 to pass through toward a reflector 92. The light, traveling from the second beam splitter 90 in the direction of the reflector 92 travels a first path length 96, which is, by way of example, fixed. The second fraction 62, traveling from the second beam splitter 90 in the direction of the adjustment reflector 94, travels a second path length 98 and an adjustment path length 97. The adjustment reflector 94 can be adjusted along the adjustment path length 97 in such a manner that the adjustment path length 97 can be varied between zero and a value larger than zero. Particularly, the adjustment path length 97 can be set according to the further difference in passage time 64 being compensated. The wavelengths of the first and the second fractions 60, 62 can be prespecified in a fixed manner by means of the first filter 58 and the second beam splitter 90.

Figure 5:
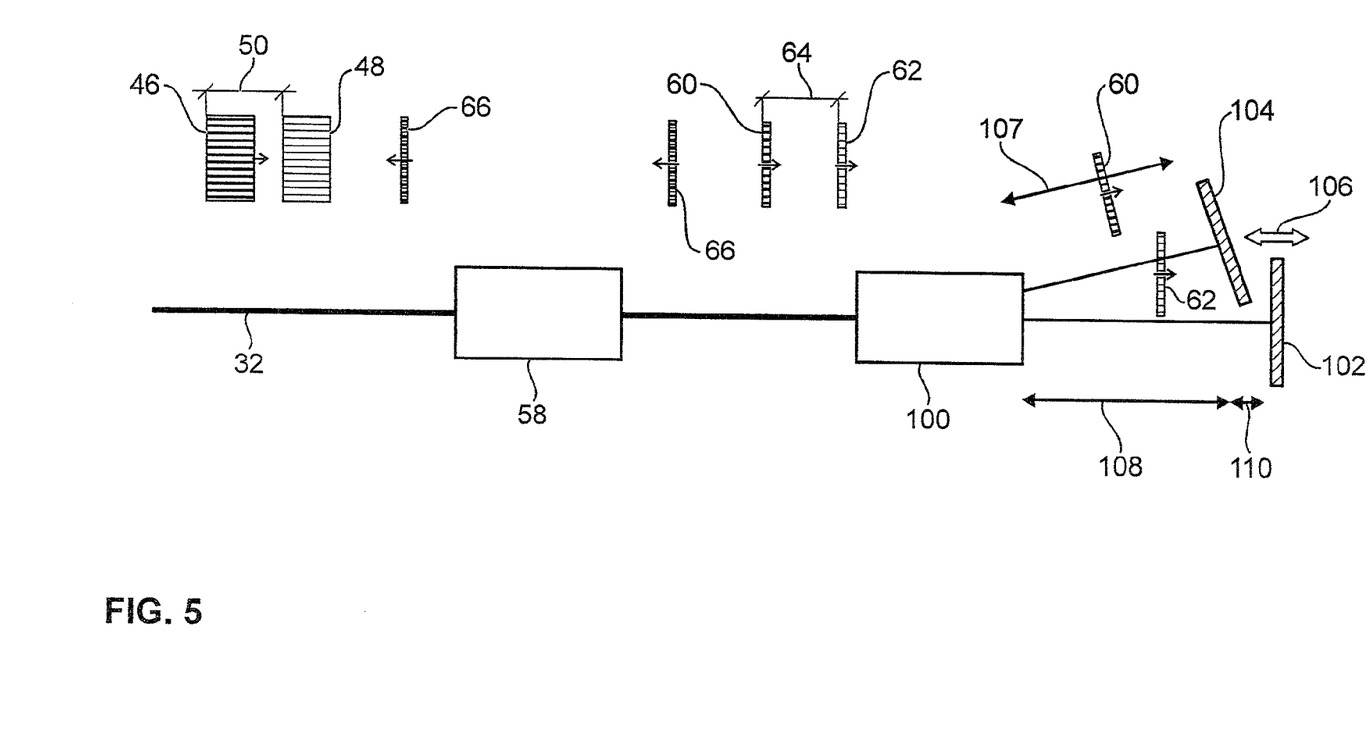
FIG. 5 shows a fifth embodiment of the compensation device.

FIG. 5 shows a further, particularly preferred embodiment of the compensation device 30. This embodiment has a second filter 100 which is, by way of example, likewise an acousto/optical filter (AOTF). The second filter 100 functions to make the first fraction 60 of the light take a different path than the second fraction 62, particularly in the direction leading to a fourth reflector 104, wherein said second fraction 62 is deflected toward a third reflector 102. The second fraction 62 travels a third path length 108 and a fourth path length 110 between the second filter 100 and the third reflector 102, wherein in this context said fourth path length 110 can also be termed the adjustment path length. Between the second filter 100 and the fourth reflector 104, the first fraction 60 of the light travels a fifth path length 107. The third reflector 102 can be moved along a third direction of movement, and the fourth path length 110 can be adjusted in this manner. In this way, the difference in path length of the fractions 60, 62 can be adjusted, and the difference in passage time can be compensated as a result. The use of the acousto/optical filter makes it possible to switch between and select the wavelengths. This means that the wavelengths of the fractions 60, 62 can be changed, and particularly can be changed quickly. The capability to rapidly change the wavelengths results from the acousto/optical filters, the same being used to change the wavelengths, having few moving parts.

Figure 6:
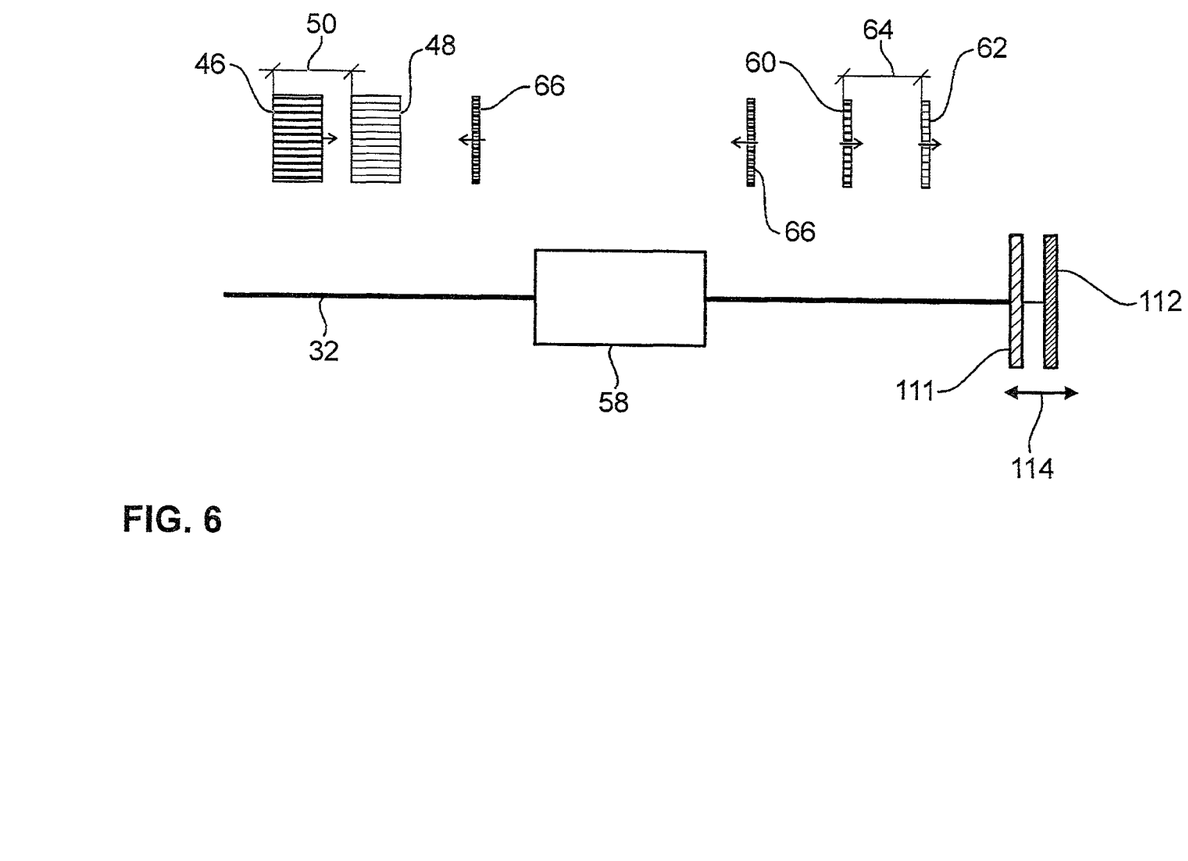
FIG. 6 shows a sixth embodiment of the compensation device of the invention.

FIG. 6 shows an embodiment of the compensation device 30, wherein the different path lengths are adjusted by means of an adjustable, partially transparent mirror surface 111. In this case, the first fraction 60 only travels the path length between the first filter 58 and the partially transparent mirror surface 111, and is then reflected. In contrast, the second fraction 62 travels the path length from the first filter 58 in the direction leading to a mirror 112, and is reflected at that point. The path traveled by the second fraction 62 is therefore longer than the path for the first fraction 60 by twice the distance between the mirror 112 and the partially transparent mirror surface 111. The partially transparent mirror surface 111, or the mirror 112, can be adjusted along an adjustment path 114, and as a result, the distance between the mirror 112 and the partially transparent mirror surface 111, and therefore the path length difference for the first and the second fractions 60, 62, can be adjusted.

The path lengths traveled in the compensation device are geometric or optical path lengths. A geometric path length corresponds to a measurable length in space. An optical path length is determined, by way of example, by a refraction index of a medium. The optical path length is therefore determined by the propagation speed of light in a medium. Compared to the path length in air, the optical path length can be longer, for example, because the light is conducted through a medium in which the propagation speed thereof is smaller than it is in air. In addition or as an alternative to the geometric path lengths which can be changed, the optical path lengths for light pulses of differing wavelengths can be selected to have different lengths and/or to be varyingly long for the purpose of compensating for the differences in passage time or for the temporal displacement of the light.

The embodiments of the compensation device 30 named above can be arranged in the laser microscope 10 as alternative devices. In addition, all named embodiments can be coupled to the sensor device 65. Furthermore, in each of the embodiments, the light packets 46, 48 or the fractions 60, 62 can be routed in parallel displacement—that is, with a positive spacing—from the combined light packet 56 and/or the mixed fractions 66. For this purpose, a mirror arrangement, for example, can be provided which can have mirrors which are tilted with respect to each other. Particularly, the step reflector 38, the adjustment mirrors 70, 72, the reflectors 92, 94, 102, 104, or the mirrors 111, 112, can be designed as 90° double reflectors which effect a parallel displacement of the incident light pulses with respect to the reflected light pulses. In addition, both adjustment mirrors 70, 72, the adjustment reflector 94, the third reflector 102, and/or the mirror surface 111 can be characterized as adjustment elements.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A laser microscope for examining a sample comprising:
   a laser light source which generates broad-band laser light pulses;
   an optical element which disperses a spectrum of the laser light pulses into fractions having different wavelengths; and
   a compensation device in which the fractions of the laser light pulses having different wavelengths travel different path lengths, such that the fractions arrive at the sample at the same time,
   wherein the compensation device comprises a beam splitter or a filter,
   wherein the beam splitter or the filter causes the fractions to travel the different path lengths, and
   wherein at least one of the different path lengths is variable, such that the fractions arrive at the sample at the same time.

2. A laser microscope according to claim 1, wherein:
   the beam splitter comprises a mirror and a semi-transparent mirror surface,
   at least one of the mirror or the mirror surface is adjustable along an adjustment path, whereby a distance between the mirror and the mirror surface changes, and
   a first fraction is reflected from the mirror surface and a second fraction is passed through the mirror surface toward the mirror and reflected from the mirror, such that the first and second fractions travel different path lengths, and the first and second fractions arrive at the sample at the same time.

3. A laser microscope according to claim 1, wherein a difference between a first path length traveled in the compensation device by a first fraction and a second path length traveled in the compensation device by a second fraction is discrete.

4. A laser microscope according to claim 1, wherein a path length traveled in the compensation device by a fraction having a prespecified wavelength is variable.

5. A laser microscope according to claim 1, wherein:
   a first fraction travels a first path length in the compensation device;
   a second fraction travels a second path length in the compensation device, and
   a wavelength of at least one of the first fraction or the second fraction is adjustable.

6. A laser microscope according to claim 1, further comprising:
   a sensor which detects a difference in passage time between the fractions, and
   an adjustment device which adjusts the path length traveled by at least one of the fractions in the compensation device depending on the difference in passage time.

7. A laser microscope according to claim 1, wherein the fractions, after traveling the different path lengths, are parallel and are displaced relative to the respective fractions before the fractions have traveled the different path lengths.

\* \* \* \* \*